(12) United States Patent
Schreiber et al.

(10) Patent No.: US 8,831,172 B2
(45) Date of Patent: Sep. 9, 2014

(54) METHOD FOR FILMLESS RADIOGRAPHIC INSPECTION OF COMPONENTS

(75) Inventors: Karl Schreiber, Am Mellensee (DE); Josef Geitner, Stahnsdorf (DE)

(73) Assignee: Rolls-Royce Deutschland Ltd & Co KG (DE)

( * ) Notice: Subject to any disclaimer, the term of this patent is extended or adjusted under 35 U.S.C. 154(b) by 473 days.

(21) Appl. No.: 13/204,444

(22) Filed: Aug. 5, 2011

(65) Prior Publication Data

US 2012/0045032 A1 Feb. 23, 2012

(30) Foreign Application Priority Data

Aug. 9, 2010 (DE) .......................... 10 2010 033 760

(51) Int. Cl.
  *G01B 15/08* (2006.01)
  *G06K 9/20* (2006.01)
  *G06K 9/60* (2006.01)
  *G01N 23/083* (2006.01)
  *G01N 23/18* (2006.01)
  *G01N 23/06* (2006.01)

(52) U.S. Cl.
  CPC ............ *G01N 23/06* (2013.01); *G01N 2223/41* (2013.01); *G01N 23/18* (2013.01)
  USPC .............. 378/58; 378/63; 378/98.5; 378/162; 382/108; 382/132; 382/141; 382/148

(58) Field of Classification Search
  CPC ....... G01B 15/08; G06K 9/20; G06K 9/2054; G06K 9/44; G06K 9/4604; G06K 9/468; G06K 9/46; G06K 9/60; G01N 23/083; G01N 23/18; G06T 7/0079
  USPC ................. 378/51, 53–63, 91, 98, 98.5, 98.8, 378/98.12, 162, 165, 204, 210; 382/128, 382/130–132, 108, 141, 145, 147, 148, 150, 382/152, 168, 171, 172, 181, 190, 192, 195, 382/204, 206, 254, 266, 276, 279, 286, 307, 382/325
  See application file for complete search history.

(56) References Cited

U.S. PATENT DOCUMENTS

| 5,289,267 A | 2/1994 | Busch |
| 6,370,223 B1 | 4/2002 | Gleason et al. |

(Continued)

FOREIGN PATENT DOCUMENTS

| DE | 10238579 | 5/2003 |
| GB | 2141822 | 1/1985 |

(Continued)

OTHER PUBLICATIONS

German Search Report dated Feb. 28, 2011 from counterpart application.

(Continued)

*Primary Examiner* — Anastasia Midkiff
(74) *Attorney, Agent, or Firm* — Timothy J. Klima; Shuttleworth & Ingersoll, PLC

(57) ABSTRACT

With filmless radiographic inspection of components by means of digital X-ray technology, an uneven surface geometry of the component is smoothened by defining a digital virtual smoothening layer for better, preferably automated, recognition of defects, where the digital radiation signals generated by an X-ray detector are overlaid with digitized surface measurement signals, so that a change in absorption and intensity of radiation due to the surface topography of the component, i.e. due to an uneven surface, is compensated for and only a density caused by internal material defects is represented in the X-ray image.

16 Claims, 1 Drawing Sheet

(56) References Cited

U.S. PATENT DOCUMENTS

Figure 1:
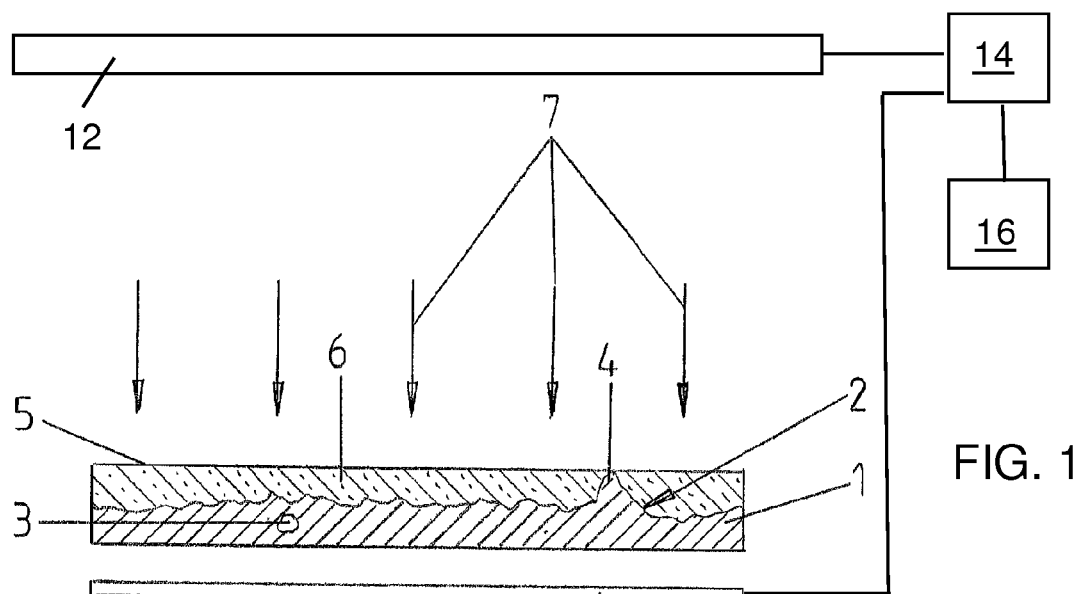

| | | |
|---|---|---|
| 6,628,746 B2 | 9/2003 | Eppler et al. |
| 2003/0099330 A1 | 5/2003 | Mery et al. |
| 2009/0003670 A1 | 1/2009 | Gu et al. |

FOREIGN PATENT DOCUMENTS

| | | |
|---|---|---|
| JP | 2005-241247 | 9/2005 |
| WO | 88/08530 | 11/1988 |
| WO | 01/63236 | 8/2001 |

OTHER PUBLICATIONS

European Search Report dated Oct. 20, 2011 from counterpart application.

Domingo Mery et al: "Automated Flaw Detection in Aluminum Castings Based on the Tracking of Potential Defects in a Radioscopic Image Sequence", IEEE Transaction on Robotics and Automation, IEEE Inc., New York, US, Bd. 18, No. 6, Dec. 1, 2002.

D. Mery and T. Jaeger: "Automatische Gussfehlererkennung: Stand der Technik", Technisches Messen, Bd. 68, No. 7-8, Jul. 2001, Seiten 338-349.

METHOD FOR FILMLESS RADIOGRAPHIC INSPECTION OF COMPONENTS

This invention relates to a method for filmless radiographic inspection of components by means of X-rays on the basis of a radiation absorption and an intensity in the radiation differing due to internal material defects, detected by a digital X-ray detector after the radiography of the component, where the digitized radiation signals are processed in a computer and generate a digitized X-ray image on a monitor.

The radiographic inspection by means of digital X-ray technology is an imaging method for non-destructive material testing, in which a component to be tested is subjected to radiation by X-rays generated by an X-ray tube, said X-rays being recorded after radiographic testing of the component by an X-ray camera (X-ray detector). During movement of the X-ray source and of the X-ray camera relative to the component (or vice versa), the signal of the X-ray detector is permanently read out and then processed and digitized in a computer in order to display a digital X-ray image of the tested workpiece on a monitor connected to the computer. Due to the differing radiation absorption and the correspondingly differing radiation attenuation, it is possible to make voids, inclusions, segregations, gas bubbles, cracks or bonding defects present in the component recognizable on the monitor in the form of a heavier density caused by the higher radiation intensity.

The detectability of material defects is impaired by edge blurring, i.e. by a penumbral area present around the imperfection, and by a low contrast (difference in density) which may be caused by scattered radiation from the electromagnetic waves impinging on an irregular component surface. However, an irregular surface structure of the component to be inspected, for example in the form of surface porosity, primarily leads to reduced radiation absorption and correspondingly high radiation intensity. The densities thus generated on the monitor do, however, not represent any relevant material defects, but rather falsify the inspection result and no longer permit any exact recognition of material defects on the monitor nor any reliable automatic evaluation of the X-ray images.

In a broad aspect, the present invention provides a method for radiographic inspection of components using digital technology that assures reliable recognition of defects present in the component material.

It is a particular object of the present invention to provide solution to the above problems by a method in accordance with the features described herein.

Advantageous developments and useful embodiments of the present invention will be apparent from the present specification.

Radiographic inspection of components using X-rays is performed on the basis of a radiation absorption altered by material defects inside the component, and of an accordingly changed intensity of the radiation signals recorded by an X-ray detector or X-ray camera after radiographic inspection of the component and generating a digital X-ray image with different grey stages on a monitor after digitization and evaluation in a computer. The core of the invention is that an uneven surface topography of the component, likewise effecting differing radiation intensities and hindering automatic evaluation of the X-ray image and reliable detection of material defects, is overlaid with a digital smoothening layer and smoothened purely by computation such that a reduction of the radiation absorption or an increase in the radiation intensity due to an uneven surface topography is compensated for, and only a density caused by internal material defects is represented in the digital X-ray image. As a result, an exact and automated radiographic inspection not influenced by surface irregularities is possible, which is of crucial importance, particularly for safety-relevant components.

The generation of the digital smoothening layer is achieved by scanning the surface of the component to be inspected with a digital X-ray scanner or laser scanner, parallel to X-ray detection with the digital X-ray camera, and overlaying the digital surface scanning signals from the scanner in the computer with the digital signals from the X-ray camera. This means that the pure surface topography signals recorded by the scanner are separated by computation from the totality of X-ray signals detected by the digital X-ray camera, such that the digital X-ray image of a component with smooth and flat surface is reproduced on the monitor, and material defects in the component such as voids, inclusions, segregations, gas bubbles, cracks or bonding defects are reliably recognized even with automatic evaluation of the digital X-ray images.

Figure 2:
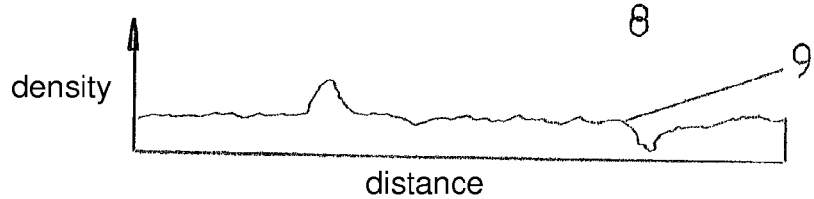
Figure 3:
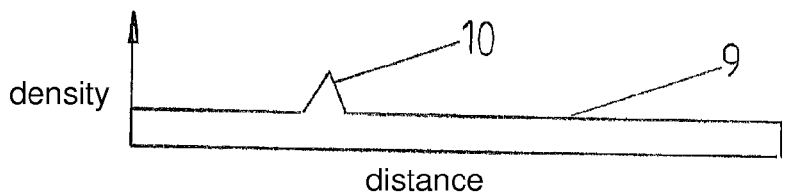

The present invention is more fully described in light of the accompanying drawings showing a preferred embodiment. In the drawings, FIG. 1 shows a component with virtual smoothening layer (3D element) during radiographic inspection, FIG. 2 shows a density image of the X-ray image without smoothening layer, FIG. 3 shows a density image of the X-ray image with virtual smoothening layer.

A component 1 made of 18.8 chrome-nickel steel, for example, has an uneven surface geometry 2 and defects 3 are to be expected in the interior of the workpiece to be tested. First the surface geometry 2 of the component 1 is measured using a measuring instrument 12, in this case a laser scanner and on the basis of the highest peak 4 ascertained a virtually smoothened surface 5 is numerically defined. The complementary 3D element 6 (virtual smoothening layer) thus created between the smooth virtual surface 5 and the uneven actual surface geometry 2 is supplemented by a specific X-ray absorption coefficient matching the component material. Then the component 1 is checked using digital X-ray technology, i.e. filmless with X-rays 7 generated by an X-ray tube and with an X-ray detector 8 (digital X-ray camera) detecting the X-rays 7 penetrating the component 1. In the computer 14, the digital radiation signals generated by the X-ray detector 8 are overlaid with the 3D element 6 generated on the basis of the digital surface measurement signals of the laser scanner 11 with the virtual surface 5, such that only an X-ray image 9 generated on the basis of a virtual smooth surface 5 and independent of any uneven surface structure is displayed on a monitor 16 connected to the computer 14. FIG. 3 is a density image/graph of the X-ray image with virtual surface smoothening, as can be shown on the monitor 16, showing a visually or automatically readily recognizable density peak 10 for indicating a defect 3 present in the component 1. FIG. 2 shows a blurred density image/graph of the X-ray image without virtual surface smoothening.

LIST OF REFERENCE NUMERALS

1 Component
2 Uneven surface geometry
3 Internal defect
4 Highest peak of 2
5 Virtually smoothened surface
6 3D element, virtual smoothening layer
7 X-rays
8 X-ray detector
9 X-ray image, density line
10 Density peak

What is claimed is:

1. A method for filmless radiographic inspection of a component, comprising:

submitting the component to radiography and creating digitized radiation signals of the component with a digital X-ray detector, processing the digitized radiation signals in a computer to generate a digitized X-ray image of the component indicating an internal defect in a material of the component, digitally recording an actual surface topography of the component to create a digitized surface topography, numerically defining a virtually smoothened surface determined by a highest peak of the digitized surface topography to create a complementary 3D element between the virtually smoothened surface and the digitized surface topography, the complementary 3D element being supplemented by an X-ray absorption coefficient specific to the material of the component, overlaying the digitized X-ray image with the complementary 3D element to produce a density image of the component independent of the actual surface topography of the component.

2. The method of claim 1, and further comprising using a digital X-ray camera as the digital X-ray detector.

3. The method of claim 2, and further comprising digitally recording the actual surface topography of the component by scanning with a laser scanner or an X-ray camera.

4. The method of claim 3, and further comprising visually recognizing defects in the material of the component.

5. The method of claim 4, wherein the defects include at least one chosen from voids, inclusions, segregations, gas bubbles, cracks and bonding defects.

6. The method of claim 3, and further comprising automatically recognizing defects in the material of the component.

7. The method of claim 4, wherein the defects include at least one chosen from voids, inclusions, segregations, gas bubbles, cracks and bonding defects.

8. The method of claim 1, and further comprising digitally recording the actual surface topography of the component by scanning with a laser scanner or an X-ray camera.

9. The method of claim 8, and further comprising visually recognizing defects in the material of the component.

10. The method of claim 9, wherein the defects include at least one chosen from voids, inclusions, segregations, gas bubbles, cracks and bonding defects.

11. The method of claim 8, and further comprising automatically recognizing defects in the material of the component.

12. The method of claim 11, wherein the defects include at least one chosen from voids, inclusions, segregations, gas bubbles, cracks and bonding defects.

13. The method of claim 1, and further comprising visually recognizing defects in the material of the component.

14. The method of claim 13, wherein the defects include at least one chosen from voids, inclusions, segregations, gas bubbles, cracks and bonding defects.

15. The method of claim 1, and further comprising automatically recognizing defects in the material of the component.

16. The method of claim 15, wherein the defects include at least one chosen from voids, inclusions, segregations, gas bubbles, cracks and bonding defects.

* * * * *